(12) United States Patent
Mikami et al.

(10) Patent No.: US 10,995,046 B2
(45) Date of Patent: May 4, 2021

(54) PROCESS FOR PRODUCING 1,2,3,4-TETRACHLOROBUTANE

(71) Applicant: SHOWA DENKO K.K., Tokyo (JP)

(72) Inventors: Katsumi Mikami, Tokyo (JP); Nozomi Kusumoto, Tokyo (JP); Shinya Oguro, Tokyo (JP); Yohsuke Fukuchi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/760,091

(22) PCT Filed: Oct. 11, 2018

(86) PCT No.: PCT/JP2018/037965
§ 371 (c)(1),
(2) Date: Apr. 29, 2020

(87) PCT Pub. No.: WO2019/106972
PCT Pub. Date: Jun. 6, 2019

(65) Prior Publication Data
US 2020/0346997 A1    Nov. 5, 2020

(30) Foreign Application Priority Data
Nov. 30, 2017 (JP) .............................. JP2017-230726

(51) Int. Cl.
*C07C 17/04* (2006.01)
(52) U.S. Cl.
CPC .................................... *C07C 17/04* (2013.01)
(58) Field of Classification Search
CPC .......... C07C 17/04; C07C 19/01; C07C 17/38
See application file for complete search history.

(56) References Cited

U.S. PATENT DOCUMENTS

2003/0028057 A1    2/2003  Owens et al.
2003/0060669 A1*   3/2003  Shibata ................... C07C 17/21
                                                570/136
(Continued)

FOREIGN PATENT DOCUMENTS

GB          1019150 A     2/1966
JP       61-000027 A     1/1986
(Continued)

OTHER PUBLICATIONS

International Search Report for PCT/JP2018/037965 dated Nov. 13, 2018 (PCT/ISA/210).
(Continued)

*Primary Examiner* — Jafar F Parsa
(74) *Attorney, Agent, or Firm* — Sughrue Mion, PLLC

(57) ABSTRACT

There is provided a method of producing 1,2,3,4-tetrachlorobutane capable of stably and economically producing 1,2,3,4-tetrachlorobutane. A reactant solution (1) containing 3,4-dichloro-1-butene is charged in a reaction vessel (11) having an inner surface, to be brought into contact with the reactant solution (1), made of a metal and a chlorine gas is introduced into the reactant solution (1) to perform a reaction between 3,4-dichloro-1-butene and the chlorine gas to produce 1,2,3,4-tetrachlorobutane. The reaction is performed while carrying out an operation of taking out at least a portion of the reactant solution (1) from the reaction vessel (11), filtering the reactant solution (1) thus taken out to remove a solid matter, and returning the filtered reactant solution (1) into the reaction vessel (11).

9 Claims, 1 Drawing Sheet

(56) References Cited

U.S. PATENT DOCUMENTS

| | | |
|---|---|---|
| 2007/0118001 A1 | 5/2007 | Bocquenet et al. |
| 2010/0121118 A1 | 5/2010 | Ohno et al. |
| 2010/0130798 A1 | 5/2010 | Ohno et al. |
| 2011/0071325 A1 | 3/2011 | Ohno et al. |
| 2014/0350309 A1 | 11/2014 | Wang et al. |
| 2015/0011804 A1 | 1/2015 | Wang et al. |

FOREIGN PATENT DOCUMENTS

| | | | |
|---|---|---|---|
| JP | 07-258122 A | 10/1995 | |
| JP | 11-240855 A | 9/1999 | |
| JP | 11-286462 A | 10/1999 | |
| JP | 2001-247494 A | 9/2001 | |
| JP | 2001-322954 A | 11/2001 | |
| JP | 2003-012578 A | 1/2003 | |
| JP | 2005-515250 A | 5/2005 | |
| JP | 2007-320972 A | 12/2007 | |
| JP | 2008-531474 A | 8/2008 | |
| JP | 5528334 B2 | 6/2014 | |
| JP | 2015-501300 A | 1/2015 | |
| JP | 2015-508818 A | 3/2015 | |
| WO | 2008/120642 A1 | 10/2008 | |
| WO | 2008/133086 A1 | 11/2008 | |
| WO | 2009/139352 A1 | 11/2009 | |
| WO | 2011058575 * | 5/2011 | ............. C07C 17/04 |

OTHER PUBLICATIONS

International Preliminary Report on Patentability dated Jun. 2, 2020 from the International Bureau in International Application No. PCT/JP2018/037965.

* cited by examiner

PROCESS FOR PRODUCING 1,2,3,4-TETRACHLOROBUTANE

This application is a National Stage of International Application No. PCT/JP2018/037965 filed Oct. 11, 2018, claiming priority based on Japanese Patent Application No. 2017-230726 filed Nov. 30, 2017.

TECHNICAL FIELD

The present invention relates to a process for producing 1,2,3,4-tetrachlorobutane.

BACKGROUND ART 1,2,3,4-tetrachlorobutane (which may hereinafter be called "TCB") is produced by chlorination of 3,4-dichloro-1-butene. TCB thus produced however solidifies in a reactant solution, depending on reaction conditions and this may prevent stable and economical production of TCB. Described specifically, TCB has optical isomers, that is, d-form, 1-form, and meso-form and the dl-form has a melting temperature of 0° C. or less and is liquid at room temperature, while the meso-form has a melting temperature of about 73° C. and is solid at room temperature. The solidification temperature of TCB therefore varies with the proportion between the meso-form and the dl-form. For example, TCB having a larger proportion of the meso-form partially solidifies at room temperature.

For example, PTL 1 describes that solidification of TCB causes a disadvantage for the industrial production of the compound and it discloses that in the reaction between TCB and fluorine, the proportion of the meso-form of TCB is desirably 60 mass % or less. When the proportion of the meso-form is 60 mass % or less, solidification of TCB can be prevented and therefore, a temperature at which TCB is dissolved in a reaction solvent and a reaction temperature can be set low.

One of the reasons for an increase in the proportion of the meso-form, depending on reaction conditions is presumed to be mixing of iron chloride and the like in the reactant solution. PTL 2 discloses that a production proportion of TCB in meso-form increases by placing, in a reaction site, a catalyst having from 0.1 to 20 mass % of iron chloride supported on a silica gel in a reaction between 3,4-dichloro-1-butene and chlorine. For suppressing an increase in the proportion of the meso-form and not causing solidification of TCB in the reaction between 3,4-dichloro-1-butene and chlorine, it has been considered to be necessary to avoid using a metal such as iron as a material of a reaction vessel in which the reaction is performed.

CITATION LIST

Patent Literatures

PTL 1: Japanese Patent No. 5528334
PTL 2: UK Patent Application Publication No. 1019150

SUMMARY OF INVENTION

Technical Problem

It was the common practice to use, as a reaction vessel in which a reaction between 3,4-dichloro-1-butene and chlorine is performed, a metallic reaction vessel or glass reaction vessel lined with a fluorine resin. Use of these reaction vessels is not industrially advantageous because they are easily damaged due to swelling of the fluorine resin or cracking of the glass.

An object of the present invention is to provide a process for producing 1,2,3,4-tetrachlorobutane capable of stably and economically producing 1,2,3,4-tetrachlorobutane.

Solution to Problem

Each aspect of the present invention for achieving the above-described object is as described below in [1] to [4].

[1] A process for producing 1,2,3,4-tetrachlorobutane by charging a reactant solution containing 3,4-dichloro-1-butene in a reaction vessel having an inner surface made of a metal, to be brought into contact with the reactant solution, and introducing a chlorine gas into the reactant solution to cause a reaction between the 3,4-dichloro-1-butene and the chlorine gas, the process including performing the reaction while taking out at least a portion of the reactant solution from the reaction vessel, filtering the portion to remove a solid matter, and returning the filtered reactant solution to the reaction vessel.

[2] The process for producing 1,2,3,4-tetrachlorobutane according to [1], wherein the metal is at least one selected from iron, iron alloys, nickel, nickel alloys, and tantalum.

[3] The process for producing 1,2,3,4-tetrachlorobutane according to [1] or [2], wherein the inner surface of the reaction vessel is subjected to at least one of polishing treatment and acid cleaning treatment.

[4] The process for producing 1,2,3,4-tetrachlorobutane according to anyone of [1] to [3], wherein the reactant solution is a solution obtained by dissolving the 3,4-dichloro-1-butene in a solvent and the solvent is at least one of 1,2,3,4-tetrachloro-1,1,2,3,4,4-hexafluorobutane and carbon tetrachloride.

Advantageous Effects of Invention

According to the present invention, 1,2,3,4-tetrachlorobutane can be produced stably and economically.

DESCRIPTION OF EMBODIMENTS

Figure 1:
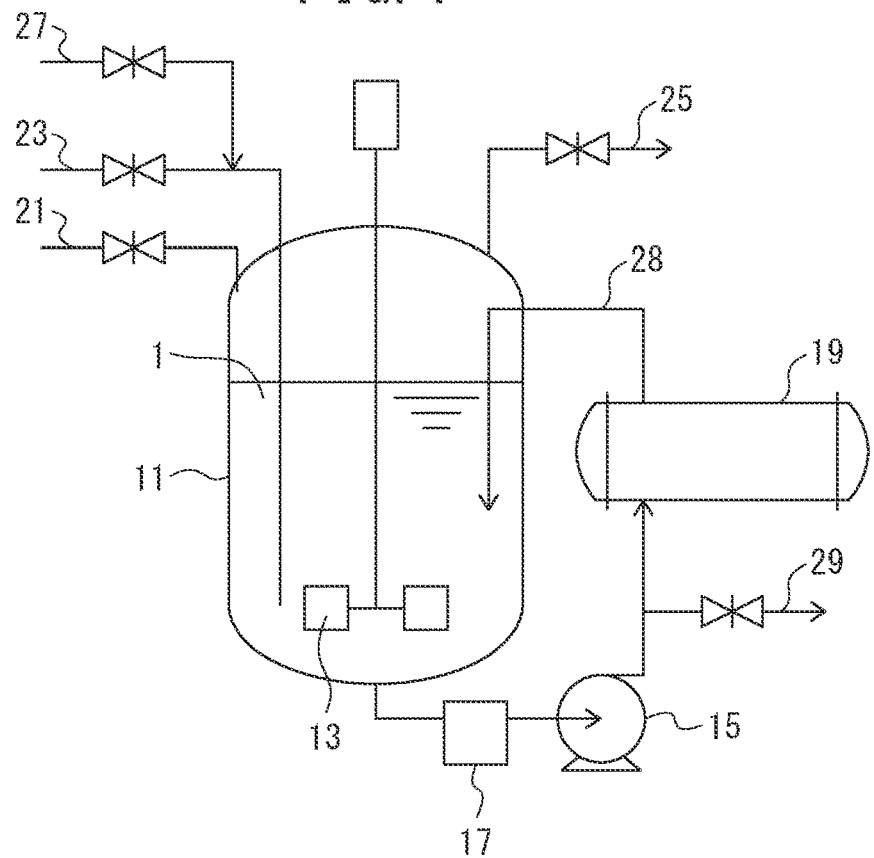
FIG. 1 is a view for describing one embodiment of the process for producing 1,2,3,4-tetrachlorobutane according to the present invention and is a schematic view for describing the constitution of a production apparatus of 1,2,3,4-tetrachlorobutane.

The embodiment of the present invention will hereinafter be described. The present embodiment shows one example of the present invention and it does not limit the present invention. Further, various changes or improvements may be added to the present embodiment and the present invention embraces the embodiment including such a change or improvement.

First, a conventional process for producing 1,2,3,4-tetrachlorobutane will be described referring to FIG. 2. A conventional production apparatus of 1,2,3,4-tetrachlorobutane illustrated in FIG. 2 includes a reaction vessel 111 in which a reaction between 3,4-dichloro-1-butene and a chlorine gas is performed, a reactant solution charging pipe 121 for introducing a reactant solution 101 containing 3,4-dichloro-1-butene into the reaction vessel 111, a stirrer 113 for stirring the reactant solution 101 in the reaction vessel 111, a chlorine gas pipe 123 for introducing a chlorine gas into the reactant solution 101 in the reaction vessel 111, and an exhaust pipe 125 for discharging a gas phase portion in the reaction vessel 111 to the outside.

A nitrogen gas pipe 127 is branched from and connected to the chlorine gas pipe 123. This makes it possible to introduce a nitrogen gas from the nitrogen gas pipe 127 into the chlorine gas pipe 123, mix the chlorine gas with the nitrogen gas to prepare a mixed gas having the chlorine gas diluted with the nitrogen gas, and introduce the mixed gas from the chlorine gas pipe 123 to the reactant solution 101.

Figure 2:
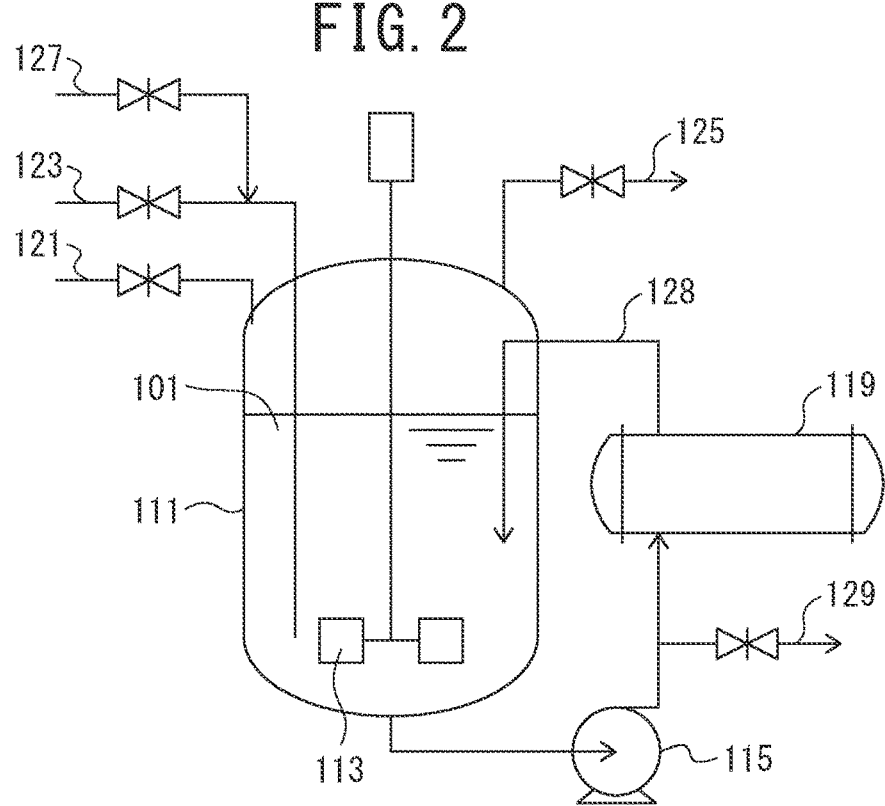
FIG. 2 is a schematic view for describing the constitution of a conventional production apparatus of 1,2,3,4-tetrachlorobutane.

Further, the production apparatus of 1,2,3,4-tetrachlorobutane illustrated in FIG. 2 includes a circulation unit for taking out a portion of the reactant solution 101 in the reaction vessel 111 during the reaction to the outside of the reaction vessel 111 and returning it into the reaction vessel 111. Described specifically, a cyclic circulation pipe 128 is connected at both ends to the reaction vessel 111 to enable, by means of a liquid circulation pump 115 installed at the circulation pipe 128, delivery of the reactant solution 101 and returning of the reactant solution 101 taken out from the reaction vessel 111 into the reaction vessel 111 via the circulation pipe 128. The circulation pipe 128 may have a heat exchanger 119, for example, downstream of the liquid circulation pump 115.

Further, a reactant solution takeout pipe 129 is branched from and connected to the circulation pipe 128. This makes it possible to take out the reactant solution 101 from the production apparatus of 1,2,3,4-tetrachlorobutane without returning it into the reaction vessel 111.

The reaction vessel 111 of the conventional production apparatus of 1,2,3,4-tetrachlorobutane illustrated in FIG. 2 is made of a stainless steel SUS316 and the inner surface of it to be brought into contact with the reactant solution 101 or a portion to be brought into contact with a gas of the gas phase portion is lined with a fluorine resin.

When a reaction was carried out using the production apparatus of 1,2,3,4-tetrachlorobutane illustrated in FIG. 2 and the mixed gas was blown into the reactant solution 101 (3,4-dichloro-1-butene), the reaction proceeded almost stably to form TCB. The proportion of TCB in meso-form was 51 mass %.

When TCB was produced by repeatedly using the production apparatus of 1,2,3,4-tetrachlorobutane illustrated in FIG. 2, however, smooth flow of the reactant solution 101 in the circulation pipe 128 was prevented and the heat of reaction was not removed sufficiently, leading to a failure in control of the reaction temperature. A shell and tube type heat exchanger 119 made of a fluorine resin was opened and checked. Then, the tube of the heat exchanger 119 was swollen with 3,4-dichloro-1-butene and had a hole due to explosion of the fluorine resin at a blocked part of the tube. In addition, water serving as a refrigerant of the heat exchanger 119 mixed in the reaction vessel 111. As a result of analysis of the reaction product TCB, the proportion of the meso-form reached as high as 75 mass %.

Such a solidification problem occurs because of the following reason. The reaction between 3,4-dichloro-1-butene and chlorine is usually performed at a temperature of from 60 to 70° C. At a reaction temperature of 60° C. or more, the meso-form does not precipitate during the reaction and clogging of the pipe or the like does not occur, while at a reaction temperature of 70° C. or less, a reduction in yield due to the polymerization reaction of 3,4-dichloro-1-butene is small.

Since the chlorination reaction of 3,4-dichloro-1-butene is an exothermic reaction, it is preferred to remove the heat of reaction to keep the temperature of the reactant solution 101 within the above-described range. When the reactant solution 101 is circulated outside the reaction vessel 111 and delivered to the heat exchanger 119 to remove the heat of reaction, there appears a portion having a temperature lower than that of the reactant solution 101 before circulation and delivery. At this time, solidification of TCB inevitably occurs in the heat exchanger 119 when the content of the meso-form in TCB is large.

Repeated use causes the solidification problem in the reaction in the reaction vessel 111 lined with a fluorine resin presumably because of the following reason. The surface made of iron is exposed to the reactant solution 101 due to breakage of the fluorine resin lining for some reason or other and it reacts with chlorine to form a solid matter containing iron chloride. This solid matter floats in the reactant solution 101 and the proportion of the meso-form in TCB increases, making solidification of TCB easy.

This solidification of TCB can be prevented by avoiding continuous use of the reaction vessel 111 lined with a fluorine resin and carrying out periodical check, but such a measure is not economical. The problem, that is, solidification of TCB can be overcome by finding conditions under which TCB can be produced without solidification during cooling. More specifically, it can be overcome by finding conditions under which the proportion of TCB in meso-form can be controlled to 65 mass % or less. When the proportion of the meso-form is more than 65 mass %, the meso-form is easily precipitated as a solid during cooling and a problem such as clogging occurs frequently.

The increase in the proportion of the meso-form is presumed to result from, as already described above, mixing of a solid matter including iron chloride and the like in the reactant solution. When a reaction vessel made of iron is used, a rough surface portion of the iron of the reaction vessel is etched by chlorine used for the reaction, floats in the reactant solution, and serves as a catalyst to increase the proportion of the meso-form.

As a result of various investigations, the present inventors have found that even if an economical reaction vessel made of iron is used, the solidification problem can be avoided without increasing the proportion of the meso-form by having a device capable of circulating the reactant solution and filtering out a solid matter.

In short, the process for producing 1,2,3,4-tetrachlorobutane according to the present embodiment includes, in producing 1,2,3,4-tetrachlorobutane by charging a reactant solution containing 3,4-dichloro-1-butene in a reaction vessel whose inner surface to be brought into contact with the reactant solution is made of a metal and introducing a chlorine gas into the reactant solution to carry out a reaction between the 3,4-dichloro-1-butene and the chlorine gas, performing the reaction while taking out at least a portion of the reactant solution from the reaction vessel, filtering the reactant solution thus taken out to remove a solid matter, and returning the filtered reactant solution to the reaction vessel.

By performing the reaction between 3,4-dichloro-1-butene and chlorine while delivering the reactant solution through a filtering unit to remove a solid matter present in the reactant solution, it is possible to suppress occurrence of an inconvenience such as clogging of a pipe even if a reaction vessel having a metallic inner surface is used. The process for producing 1,2,3,4-tetrachlorobutane according to the present embodiment therefore makes it possible to stably and economically produce TCB.

1,2,3,4-Tetrachlorobutane can be used as a raw material for synthesizing hexafluoro-1,3-butadiene via 1,2,3,4-tetrachloro-1,1,2,3,4,4-hexafluorobutane. Since hexafluoro-1,3-butadiene is used in a large amount as an etching gas in a semiconductor manufacturing step, a process for stably and economically producing TCB is very useful.

Use of a reaction vessel lined with a fluorine resin is not required in the present embodiment and the inner surface of a reaction vessel may be made of a metal. As the metal used for formation of the inner surface of a reaction vessel, that having corrosion resistance against a chlorine gas, hydrogen chloride, or hydrochloric acid is preferred. At least one metal selected from iron, iron alloys, nickel, nickel alloys, and tantalum can be mentioned as an example of it. These metals may be used either singly or in combination of two or more. Examples of the iron alloys include stainless steels such as SUS316L and those of the nickel alloys include Hastelloy (trade mark) and Monel (trade mark).

The inner surface of a reaction vessel may be subjected to at least one of polishing treatment and acid cleaning treatment. Examples of the polishing treatment include polishing treatment with polishing paper having a polishing material with a grain size larger than P150. Examples of the acid cleaning treatment include surface cleaning treatment with an acid such as nitric acid or sulfuric acid. Even a metal surface of the 1,2,3,4-tetrachlorobutane production apparatus other than the inner surface of the reaction vessel may be subjected to at least one of polishing treatment and acid cleaning treatment.

If the inner surface of the reaction vessel or a metal surface of another portion has rust or dirt, the rust or dirt peels off, floats in the reactant solution and then, is supplied to a site where a reaction mainly occurs due to a chlorine gas blown into the reactant solution. When the rust or dirt is, for example, an iron-containing substance, it reacts with water and hydrogen chloride and becomes iron oxide or it reacts with the chlorine gas and becomes iron chloride. The iron oxide or iron chloride thus formed shows catalytic action and increases the production proportion of the meso-form.

The filtering unit for circulating the reactant solution and filtering out a solid matter is not particularly limited and examples include a filter and a precipitation and filtering device. A device using a filter for removing a solid matter is the most simple and convenient one. As the filter, a filter cloth or a porous plate through which not a solid matter but a liquid passes can be used. In addition, a filter made of a material having a substance eluted into the reactant solution as less as possible is preferred. Examples of a preferred filter material include a filter cloth made of glass fiber or a synthetic fiber such as polyester, polyamide, polyolefin, aramid, acrylic resin, fluorine resin, polyphenylene sulfide, or polyimide and a sintered metal.

A circulation amount of the reactant solution is not particularly limited because it varies with an amount of the reactant solution, a blowing amount of a chlorine gas, capacity of the heat exchanger, or the like but an hourly circulation amount of the solution is adjusted to preferably from 5 times or more to 1000 times or less the amount of the reactant solution charged in the reaction vessel, more preferably from 10 times or more to 100 times or less. The circulation amount within the above-described range is economical because a heat exchanger having particularly high cooling capacity or a pump having particularly high feeding capacity is not required.

The purity of 3,4-dichloro-1-butene, a raw material, is preferably 90 mass % or more.

The reaction between 3,4-dichloro-1-butene and a chlorine gas may be performed in a solvent or in a solventless manner. The reaction in a solventless manner is performed using 3,4-dichloro-1-butene as a reactant solution and introducing a chlorine gas into the reactant solution. The reaction in a solvent is performed using, as a reactant solution, a solution obtained by dissolving 3,4-dichloro-1-butene in a solvent and introducing a chlorine gas into the reactant solution. Although the kind of the solvent is not particularly limited, at least one of 1,2,3,4-tetrachloro-1,1,2,3,4,4-hexafluorobutane and carbon tetrachloride may be used.

The production proportion of the meso-form in TCB does not change, depending on the presence or absence of the solvent and a solidification temperature of the meso-form differs with the concentration of the meso-form in the reactant solution. The amount of the solvent is therefore adjusted according to a temperature at which the reactant solution is handled.

A water content in the reactant solution is preferably less than a saturated solubility of water of the reactant solution, more preferably 100 mass ppm or less. When the water content is equal to or more than the saturated solubility, a water layer is present on the surface of the reactant solution. It is not preferred to perform a chlorination reaction with the water layer present on the surface of the reactant solution, because chlorine or by-produced hydrochloric acid dissolves in this water layer to form an acidic water solution and the resulting solution corrodes the metal forming the reaction vessel. When the reaction vessel is corroded and a metal oxide or chloride thus formed peels off and floats in the reactant solution, such an oxide or chloride shows catalytic action and may cause an increase in the production proportion of the meso-form, an optical isomer.

Although the concentration of the chlorine gas used for the reaction is not particularly limited, when a chlorine gas diluted with an inert gas such as nitrogen gas or argon is used, it is preferred to attach the reaction vessel with a pipe for discharging an exhaust gas from the gas phase portion of the reaction vessel.

The chlorination reaction is an exothermic reaction so that the production apparatus of 1,2,3,4-tetrachlorobutane may include a heat exchanger for removing the heat of reaction to keep the temperature of the reactant solution constant. In addition, to achieve a uniform reaction between the reactant solution and the blown chlorine gas, the reaction vessel has preferably a stirrer equipped with a stirring blade for stirring the reactant solution.

Further, the reaction vessel may be equipped with a pump and pipe for circulating the reactant solution, a chlorine gas pipe for introducing a chlorine gas into the reactant solution, an exhaust pipe for discharging the gas phase portion in the reaction vessel to the outside of the reaction vessel, a reactant solution charging pipe for introducing the reactant solution into the reaction vessel, and a reactant solution takeout pipe for taking out the reactant solution from the reaction vessel.

Still further, the production apparatus of 1,2,3,4-tetrachlorobutane may be equipped with a general instrument necessary for operating the production apparatus of 1,2,3,4-tetrachlorobutane such as a temperature measuring unit for measuring the temperature of the reactant solution, for example, a thermocouple, a pressure gauge for measuring the pressure of each site in the reaction vessel or the like, and a flow meter for measuring the flow rate of a solution passing through the pipe.

EXAMPLES

The present invention will hereinafter be described in further detail by Examples and Comparative Examples.

Example 1

First, the constitution of the production apparatus of 1,2,3,4-tetrachlorobutane used in Example 1 will be described referring to FIG. 1. The production apparatus of 1,2,3,4-tetrachlorobutane illustrated in FIG. 1 includes a reaction vessel 11 in which a reaction is performed between 3,4-dichloro-1-butene and a chlorine gas, a reactant solution charging pipe 21 for introducing a reactant solution 1 containing 3,4-dichloro-1-butene into the reaction vessel 11, a stirrer 13 for stirring the reactant solution 1 in the reaction vessel 11, a chlorine gas pipe 23 for introducing a chlorine gas into the reactant solution 1 in the reaction vessel 11, and an exhaust pipe 25 for discharging a gas phase portion in the reaction vessel 11 to the outside.

A nitrogen gas pipe 27 is branched from and connected to the chlorine gas pipe 23, making it possible to introduce a nitrogen gas from the nitrogen gas pipe 27 to the chlorine gas pipe 23 to mix the chlorine gas with the nitrogen gas, prepare a mixed gas in which the chlorine gas has been diluted with the nitrogen gas, and introduce the mixed gas into the reactant solution 1 from the chlorine gas pipe 23.

The production apparatus of 1,2,3,4-tetrachlorobutane illustrated in FIG. 1 further includes a circulation equipment for taking out a portion of the reactant solution 1 in the reaction vessel 11 during the reaction to the outside of the reaction vessel 11, carrying out treatment such as filtration, and then returning the residue into the reaction vessel 11. Described specifically, a cyclic circulation pipe 28 is connected at both ends to the reaction vessel 11 to enable, by means of a liquid circulation pump 15 installed at the circulation pipe 28, delivery of the reactant solution 1 and returning of the reactant solution 1 taken out from the reaction vessel 11 into the reaction vessel 11 via the circulation pipe 28.

The reaction vessel 11 and the liquid circulation pump 15 have a filtering unit 17 between them so as to remove a solid matter from the reactant solution 1 taken out from the vessel. The filtered reactant solution 1 passes through the heat exchanger 19 and then is returned into the reaction vessel 11. In other words, the production apparatus of 1,2,3,4-tetrachlorobutane illustrated in FIG. 1 is configured to carryout a reaction while taking out a portion of the reactant solution 1 from the reaction vessel 11, filtering the reactant solution 1 taken out from the vessel to remove a solid matter, and returning the thus-filtered reactant solution 1 to the reaction vessel 11.

Further, a reactant solution takeout pipe 29 is branched from and connected to the circulation pipe 28 on the downstream side of the filtering unit 17. The filtered reactant solution 1 can therefore be taken out from the reaction vessel 11 without returning it into the reaction vessel 11.

The reaction vessel 11 has an inner diameter of 1 m and a height of 0.9 m. The surface of the reactant solution 1 poured in the reaction vessel 11 has an area of 0.78 m$^2$. The entire reaction vessel 11 including the inner surface is made of a stainless steel SUS316. Prior to use of the production apparatus of 1,2,3,4-tetrachlorobutane for the reaction, the inner surface of the reaction vessel 11 is polished with polishing paper having a polishing material with a grain size larger than P240, cleaned with an acid, and then dried in a nitrogen gas stream.

The reaction was performed using the production apparatus of 1,2,3,4-tetrachlorobutane as described above to produce 1,2,3,4-tetrachlorobutane. The reaction vessel 11 was charged with 550 kg of 3,4-dichloro-1-butene as the reactant solution 1 and after adjustment of the solution temperature to 70° C., a chlorine gas having a concentration of 100 mol % was supplied to the reactant solution 1 at a flow rate of 54 kg/h to cause a chlorination reaction. During the reaction, the reactant solution 1 was fed to the filtering unit 17 at a flow rate of 14700 kg/h and circulated. In other words, the reactant solution 1 was fed to the filtering unit 17 via the circulation pipe 28 to filter out a solid matter and the reactant solution 1 after passing the filtering unit 17 was returned to the reaction vessel 11. The temperature of the reactant solution 1 during the reaction was kept at 70° C. The water content in the reactant solution 1 was 10 mass ppm.

After the reaction was performed for about 5.7 hours, supply of the chlorine gas was stopped. During the reaction, there occurred neither clogging of pipes such as the circulation pipe 28 with a solid matter nor liquid leakage from the reaction vessel 11 or pipes such as the circulation pipe 28. Analysis of the reactant solution 1 after the supply of the chlorine gas was stopped revealed that a rate of reaction of 3,4-dichloro-1-butene was 100% and a yield of TCB was 97 mol %. The proportion of the meso-form in the resulting TCB was 50 mass %. The yield of TCB and proportion of the meso-form in TCB were determined by quantitative analysis (internal standard method) of the reactant solution 1 by using gas chromatography.

Comparative Example 1

In a manner similar to that of Example 1 except that the production apparatus of 1,2,3,4-tetrachlorobutane did not include a filtering unit and 550 g of water was added to form a water layer on the surface of the reactant solution, the reaction was performed.

Analysis of the reactant solution after supply of a chlorine gas was stopped revealed that a rate of reaction of 3,4-dichloro-1-butene was 100% and a yield of TCB was 97 mol %. The proportion of the meso-form in the resulting TCB was 70 mass %. As a result of inspection of the inside of the reaction vessel, corrosion occurred at a portion of the inner surface of the reaction vessel in contact with the gas phase portion. A powdery substance presumed to result from corrosion remained on the bottom of the reaction vessel and the analysis of it showed that it was a mixture of iron oxide and iron chloride.

Comparative Example 2

In a manner similar to that of Example 1 except that the production apparatus of 1,2,3,4-tetrachlorobutane did not include a filtering unit and the reaction was performed by adding 5 g of iron oxide (III) powder, the reaction was performed.

Analysis of the reactant solution after supply of the chlorine gas was stopped revealed that a rate of reaction of 3,4-dichloro-1-butene was 100% and a yield of TCB was 97 mol %. The proportion of the meso-form in the resulting TCB was 75 mass %.

Example 2

In a manner similar to that of Example 1 except that the reaction was performed by adding 5 g of iron oxide (III) powder, the reaction was performed.

Analysis of the reactant solution 1 after supply of a chlorine gas was stopped revealed that the rate of reaction of 3,4-dichloro-1-butene was 100% and the yield of TCB was 97 mol %. The proportion of the meso-form in the resulting TCB was 55 mass %. As a result of inspection of the inside of the reaction vessel 11, the iron oxide (III) powder thus added and an iron chloride powder derived from the reaction of the iron oxide (III) with chlorine were removed by the filtering unit and no powder was found on the bottom of the reaction vessel 11.

Comparative Example 3

In a manner similar to that of Example 1 except that the production apparatus of 1,2,3,4-tetrachlorobutane did not include a filtering unit and the inner surface of the reaction vessel was subjected to neither polishing nor acid cleaning, the reaction was performed.

Analysis of the reactant solution after supply of the chlorine gas was stopped revealed that the rate of reaction of 3,4-dichloro-1-butene was 100% and the yield of TCB was 97 mol %. The proportion of the meso-form in the resulting TCB was 67 mass %.

Comparative Example 4

In a manner similar to that of Example 1 except that the production apparatus of 1,2,3,4-tetrachlorobutane did not include a filtering unit and the reaction was performed by adding 5 g of an iron oxide (III) powder and 550 g of water, the reaction was performed.

Analysis of the reactant solution after supply of the chlorine gas was stopped revealed that the rate of reaction of 3,4-dichloro-1-butene was 100% and the yield of TCB was 97 mol %. The proportion of the meso-form in the resulting TCB was 79 mass %.

Example 3

In a manner similar to that of Example 1 except that 550 g of water was added to form a water layer on the surface of the reactant solution 1, the reaction was performed.

Analysis of the reactant solution 1 after supply of the chlorine gas was stopped revealed that the rate of reaction of 3,4-dichloro-1-butene was 100% and the yield of TCB was 97 mol %. The proportion of the meso-form in the resulting TCB was 61 mass %. As a result of inspection of the inside of the reaction vessel 11, an iron chloride powder generated during the reaction was removed by the filtering unit 17 and no powder was found on the bottom of the reaction vessel 11.

Example 4

In a manner similar to that of Example 1 except that 5 g of an iron oxide (III) power and 550 g of water were added, the reaction was performed.

Analysis of the reactant solution 1 after supply of the chlorine gas was stopped revealed that the rate of reaction of 3,4-dichloro-1-butene was 100% and the yield of TCB was 97 mol %. The proportion of the meso-form in the resulting TCB was 63 mass %. As a result of inspection of the inside of the reaction vessel 11, the iron oxide (III) powder added and an iron chloride powder derived from a reaction of the iron oxide (III) with chlorine were removed by the filtering unit 17 and no powder was found on the bottom of the reaction vessel 11.

TABLE 1

| | Filtering unit | Iron oxide powder | Water layer | Meso form (mass %) | Iron chloride powder on bottom of reaction vessel | Corrosion of inner surface of reaction vessel |
| --- | --- | --- | --- | --- | --- | --- |
| Ex. 1 | Included | Not added | Not formed | 50 | None | Not found |
| Ex. 2 | Included | Added | Not formed | 55 | None | Not found |
| Ex. 3 | Included | Not added | Formed | 61 | None | Not found |
| Ex. 4 | Included | Added | Formed | 63 | None | Not found |
| Comp. Ex. 1 | Not included | Not added | Formed | 70 | Remained | Found |
| Comp. Ex. 2 | Not included | Added | Not formed | 75 | Remained | Found |
| Comp. Ex. 3 | Not included | Not added | Not formed | 67 | Remained | Found |
| Comp. Ex. 4 | Not included | Added | Formed | 79 | Remained | Found |

The reaction conditions and evaluation results are both listed in Table 1. As is apparent from Table 1, in Examples 1 to 4 compared with Comparative Examples 1 to 4, the proportion of the meso-form in the resulting TCB is as low as 65 mass % or less, making it possible to cause neither formation of an iron chloride powder on the bottom of the reaction vessel 11 nor corrosion of the inner surface of the reaction vessel 11.

REFERENCE SIGNS LIST 1, 101: Reactant solution
11, 111: Reaction vessel
13, 113: Stirrer
15, 115: Liquid circulation pump
17: Filtering unit
19, 119: Heat exchanger
21, 121: Reactant solution charging pipe
23, 123: Chlorine gas pipe
25, 125: Exhaust pipe
27, 127: Nitrogen gas pipe
28, 128: Circulation pipe
29, 129: Reactant solution takeout pipe

The invention claimed is:
1. A process for producing 1,2,3,4-tetrachlorobutane by charging a reactant solution containing 3,4-dichloro-1-butene in a reaction vessel having an inner surface made of a metal, to be brought into contact with the reactant solution and introducing a chlorine gas into the reactant solution to cause a reaction between the 3,4-dichloro-1-butene and the chlorine gas, the process comprising performing the reaction while taking out at least a portion of the reactant solution from the reaction vessel, filtering the portion to remove a solid matter, and returning the filtered reactant solution to the reaction vessel.

2. The process for producing 1,2,3,4-tetrachlorobutane according to claim 1, wherein the metal is at least one selected from iron, iron alloys, nickel, nickel alloys, and tantalum.

3. The process for producing 1,2,3,4-tetrachlorobutane according to claim 1, wherein the inner surface of the reaction vessel is subjected to at least one of polishing treatment and acid cleaning treatment.

4. The process for producing 1,2,3,4-tetrachlorobutane according to claim 1, wherein the reactant solution is a solution obtained by dissolving the 3,4-dichloro-1-butene in a solvent and the solvent is at least one of 1,2,3,4-tetrachloro-1,1,2,3,4,4-hexafluorobutane and carbon tetrachloride.

5. The process for producing 1,2,3,4-tetrachlorobutane according to claim 2, wherein the inner surface of the reaction vessel is subjected to at least one of polishing treatment and acid cleaning treatment.

6. The process for producing 1,2,3,4-tetrachlorobutane according to claim 2, wherein the reactant solution is a solution obtained by dissolving the 3,4-dichloro-1-butene in a solvent and the solvent is at least one of 1,2,3,4-tetrachloro-1,1,2,3,4,4-hexafluorobutane and carbon tetrachloride.

7. The process for producing 1,2,3,4-tetrachlorobutane according to claim 3, wherein the reactant solution is a solution obtained by dissolving the 3,4-dichloro-1-butene in a solvent and the solvent is at least one of 1,2,3,4-tetrachloro-1,1,2,3,4,4-hexafluorobutane and carbon tetrachloride.

8. The process for producing 1,2,3,4-tetrachlorobutane according to claim 1, wherein the reaction vessel has a stirrer equipped with a stirring blade for stirring the reactant solution.

9. The process for producing 1,2,3,4-tetrachlorobutane according to claim 1, wherein the filtering is with a filter made of a filter material selected from the group consisting of (i) a filter cloth made of glass fiber or a synthetic fiber, wherein the synthetic fiber is polyester, polyamide, polyolefin, aramid, acrylic resin, fluorine resin, polyphenylene sulfide, or polyimide, and (ii) a sintered metal.

* * * * *